(12) United States Patent
Bhattacharyya et al.

(10) Patent No.: US 8,933,265 B2
(45) Date of Patent: Jan. 13, 2015

(54) PROCESS FOR OXIDIZING ALKYL AROMATIC COMPOUNDS

(75) Inventors: Alakananda Bhattacharyya, Glen Ellyn, IL (US); Joel T. Walenga, Lake Zurich, IL (US)

(73) Assignee: UOP LLC, Des Plaines, IL (US)

(*) Notice: Subject to any disclaimer, the term of this patent is extended or adjusted under 35 U.S.C. 154(b) by 885 days.

(21) Appl. No.: 13/155,663

(22) Filed: Jun. 8, 2011

(65) Prior Publication Data

US 2012/0004448 A1 Jan. 5, 2012

Related U.S. Application Data

(60) Provisional application No. 61/360,281, filed on Jun. 30, 2010.

(51) Int. Cl.
*C07C 51/16* (2006.01)
*C07C 51/265* (2006.01)

(52) U.S. Cl.
CPC .................................... *C07C 51/265* (2013.01)
USPC ........................................................ 562/408

(58) Field of Classification Search
CPC ................................ C07C 63/15; C07C 61/15
USPC ........................................................ 562/408
See application file for complete search history.

(56) References Cited

U.S. PATENT DOCUMENTS

| | | | |
|---|---|---|---|
| 2,833,816 A | 5/1958 | Saffer | |
| 3,299,125 A | 1/1967 | Ichikawa | |
| 3,584,039 A | 6/1971 | Meyer | |
| 3,726,915 A | 4/1973 | Pohlmann | |
| 3,947,494 A | 3/1976 | Kuhlmann | |
| 4,323,699 A | 4/1982 | Norval | |
| 4,330,676 A | 5/1982 | Moxham | |
| 4,380,662 A | 4/1983 | Hanotier | |
| 4,394,299 A | 7/1983 | Puskas | |
| 4,853,479 A | 8/1989 | Dakka | |
| 4,965,406 A | 10/1990 | Dakka | |
| 5,081,290 A | 1/1992 | Partenheimer | |
| 5,095,146 A | 3/1992 | Zeitlin et al. | |
| 5,200,557 A | 4/1993 | Gee et al. | |
| 5,354,898 A | 10/1994 | Schroeder | |
| 6,137,001 A | 10/2000 | Broeker et al. | |
| 6,303,827 B1 | 10/2001 | Saleh et al. | |
| 6,320,083 B1 | 11/2001 | Saleh et al. | |
| 6,355,835 B1 | 3/2002 | Kulsrestha et al. | |
| 6,562,996 B2 | 5/2003 | Saleh | |
| 7,094,925 B2 * | 8/2006 | Earle et al. | 562/410 |
| 7,196,215 B2 | 3/2007 | Lin | |
| 7,449,596 B2 | 11/2008 | Campbell et al. | |
| 7,488,843 B1 | 2/2009 | Lee et al. | |
| 7,538,237 B2 | 5/2009 | Holl et al. | |
| 7,692,036 B2 | 4/2010 | Wonders et al. | |
| 2006/0116530 A1 | 6/2006 | Wonders | |
| 2007/0010688 A1 | 1/2007 | Ko | |
| 2007/0129568 A1 | 6/2007 | Flanagan et al. | |
| 2009/0326265 A1 * | 12/2009 | Hashmi et al. | 562/416 |
| 2010/0174111 A1 | 7/2010 | Rogers et al. | |

FOREIGN PATENT DOCUMENTS

WO 2008151034 A1 12/2008

OTHER PUBLICATIONS

International Search Report and Written Opinion for PCT/US2011/040502 mailed Feb. 21, 2012, Intl. filing date Jun. 15, 2011, Bhattacharyya.
International Preliminary Report on Patentability (IPRP) for PCT/US2011/040502 mailed Jan. 17, 2013, Intl. filing date Jun. 15, 2011, Bhattacharyya.
International Search Report and Written Opinion for PCT/US2011/040515 mailed Feb. 21, 2012, Intl. filing date Jun. 15, 2011, Bhattacharyya.
International Preliminary Report on Patentability (IPRP) for PCT/US2011/040515 mailed Jan. 17, 2013, Intl. filing date Jun. 15, 2011, Bhattacharyya.
International Search Report and Written Opinion for PCT/US2011/040467 mailed Feb. 21, 2012, Intl. filing date Jun. 15, 2011, Bhattacharyya.
International Preliminary Report on Patentability (IPRP) for PCT/US2011/040467 mailed Jan. 17, 2013, Intl. filing date Jun. 15, 2011, Bhattacharyya.
International Search Report and Written Opinion for PCT/US2011/040601 mailed Jan. 18, 2012, Intl. filing date Jun. 16, 2011, Bhattacharyya.
International Preliminary Report on Patentability (IPRP) for PCT/US2011/040601 mailed Jan. 17, 2013, Intl. filing date Jun. 16, 2011, Bhattacharyya.

(Continued)

*Primary Examiner* — Sudhakar Katakam
*Assistant Examiner* — Kofi Adzamli

(57) ABSTRACT

A process and a mixture for oxidizing an alkyl-aromatic compound comprises forming a mixture comprising the alkyl-aromatic compound, a solvent, a bromine source, a catalyst, and ammonium acetate; and contacting the mixture with an oxidizing agent at oxidizing conditions to produce an oxidation product comprising at least one of an aromatic aldehyde, an aromatic alcohol, an aromatic ketone, and an aromatic carboxylic acid. The solvent comprises a carboxylic acid having from 1 to 7 carbon atoms; and the catalyst comprises at least one of cobalt, titanium, manganese, chromium, copper, nickel, vanadium, iron, molybdenum, tin, cerium, and zirconium.

7 Claims, No Drawings

(56) References Cited

OTHER PUBLICATIONS

International Search Report and Written Opinion for PCT/US2011/040602 mailed Jan. 18, 2012, Intl. filing date Jun. 16, 2011, Bhattacharyya.
International Preliminary Report on Patentability (IPRP) for PCT/US2011/040602 mailed Jan. 17, 2013, Intl filing date Jun. 16, 2011, Bhattacharyya.
Interntional Search Report and Written Opinion for PCT/US2011/040474 mailed Feb. 9, 2012, Intl. filing date Jun. 15, 2011, Bhattacharyya.
International Preliminary Report on Patentability (IPRP) for PCT/US2011/040474 mailed Jan. 17, 2013, Intl. filing date Jun. 15, 2011, Bhattacharyya.
International Search Report and Written Opinion for PCT/US2011/040482 mailed Feb. 21, 2012, Intl. filing date Jun. 15, 2011, Bhattacharyya.
International Preliminary Report on Patentability (IPRP) for PCT/US2011/040482 mailed Jan. 17, 2013, Intl. filing date Jun. 15, 2011, Bhattacharyya.
U.S. Appl. No. 13/155,519, filed Jun. 8, 2011, Bhattacharyya et al.
U.S. Appl. No. 13/155,530, filed Jun. 8, 2011, Bhattacharyya et al.
U.S. Appl. No. 13/155,553, filed Jun. 8, 2011, Bhattacharyya et al.
U.S. Appl. No. 13/155,568, filed Jun. 8, 2011, Bhattacharyya et al.
U.S. Appl. No. 13/155,624, filed Jun. 8, 2011, Bhattacharyya et al.
U.S. Appl. No. 13/155,677, filed Jun. 8, 2011, Bhattacharyya et al.

* cited by examiner

PROCESS FOR OXIDIZING ALKYL AROMATIC COMPOUNDS

CROSS-REFERENCE TO RELATED APPLICATION

This application claims the benefit of U.S. Provisional Application No. 61/360,281 which was filed on Jun. 30, 2010.

FIELD OF THE INVENTION

This invention relates to processes and mixtures useful for oxidizing alkyl aromatic compounds. More particularly, the invention relates to the oxidation of alkyl aromatic compounds in the presence of a solvent, a catalyst, a bromine source, and ammonium acetate.

BACKGROUND OF THE INVENTION

The oxidation of alkyl aromatic compounds, e.g., toluene and xylenes are important commercial process. A variety of oxidation products may be obtained including aromatic carboxylic acids such as terephthalic acid (1,4-benzenedicarboxylic acid) and isophthalic acid (1,3-benzenedicarboxylic acid) which are used for example in the polymer industry.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidising in the presence of acetic acid as solvent, cobalt salt as catalyst and an initiator. The oxidation step is followed by flashing the said reaction mixture to remove volatile substances and cooling and filtering to get crude benzene di-carboxylic acid as a solid product and filtrate. Recrystallizing the crude benzene di-carboxylic acid to obtain at least 99% purity and recycling of the filtrate are also disclosed.

It is also known in the art that the oxidation products such as aromatic aldehydes, aromatic alcohols, aromatic ketones, and aromatic carboxylic acids may solidify or crystallize at oxidation conditions and/or as the reaction mixture cools. Thus, mixtures of oxidation products may be produced which require further processing to increase the purity of the desired product. For example, in the production of terephthalic acid, the oxidation product is often referred to as crude terephthalic acid as it contains impurities including color bodies and intermediate oxidation products especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 7,692,036 discloses an optimized process and apparatus for more efficiently and economically carrying out the liquid-phase oxidation of an oxidizable compound. Such liquid-phase oxidation is carried out in a bubble column reactor that provides for a highly efficient reaction at relatively low temperatures. When the oxidized compound is para-xylene and the product from the oxidation reaction is crude terephthalic acid (CTA), such CTA product can be purified and separated by more economical techniques than could be employed if the CTA were formed by a conventional high-temperature oxidation process.

There remains a need in the art for alternate processes that enable the oxidation of alkyl aromatic compounds including oxidation processes that produce aromatic carboxylic acids. Oxidation processes that produce higher purity oxidation products are desirable to eliminate or minimize purification costs. Resulting products with different ratios of contaminant may provide new intermediates useful as raw materials in other applications.

SUMMARY OF THE INVENTION

It has been discovered that the oxidation of an alkyl-aromatic compound in the presence of ammonium acetate may provide a solid oxidation product having a different composition relative to that observed in conventional processes. In an embodiment, the invention provides a solid oxidation product of higher purity.

In an embodiment, the invention is a process for oxidizing an alkyl-aromatic compound comprising: forming a mixture comprising the alkyl-aromatic compound, a solvent, a bromine source, a catalyst, and ammonium acetate; and contacting the mixture with an oxidizing agent at oxidizing conditions to produce a solid oxidation product comprising at least one of an aromatic aldehyde, an aromatic alcohol, an aromatic ketone, and an aromatic carboxylic acid; wherein the solvent comprises a carboxylic acid having from 1 to 7 carbon atoms, and the catalyst comprises at least one of cobalt, titanium, manganese, chromium, copper, nickel, vanadium, iron, molybdenum, tin, cerium, and zirconium.

In another embodiment, the invention is a mixture for oxidizing an alkyl-aromatic compound comprising: the alkyl-aromatic compound, a solvent, a bromine source, a catalyst, and ammonium acetate; wherein the solvent comprises a carboxylic acid having from 1 to 7 carbon atoms, and the catalyst comprises at least one of cobalt, titanium, manganese, chromium, copper, nickel, vanadium, iron, molybdenum, tin, cerium, and zirconium.

DETAILED DESCRIPTION OF THE INVENTION

In general, the invention relates to processes and mixtures or compositions for the oxidation of alkyl aromatic compounds to produce one or more oxidation products, such as, aromatic aldehydes, aromatic alcohols, aromatic ketones, and aromatic carboxylic acids. Exemplary processes according to the invention include the oxidation of para-xylene to terephthalic acid, the oxidation of ortho-xylene to phthalic acid, and the oxidation of meta-xylene to isophthalic acid.

Suitable alkyl aromatic compounds or feeds to be oxidized include aromatic compounds comprising at least one benzene ring having at least one alkyl group. Methyl, ethyl, and iso-propyl alkyl groups are preferred alkyl groups but are not required. In an embodiment, the alkyl aromatic compound is selected from the group consisting of toluene, para-xylene, ortho-xylene, and meta-xylene. The feed may comprise more than one alkyl aromatic compound. As the oxidation reaction generally proceeds through successive degrees of oxidization, suitable feed compounds also include partially oxidized intermediates relative to the desired oxidized product. For example, in the production of terephthalic acid, the alkyl aromatic feed may comprise para-toluic acid and/or 4-carboxybenzaldehyde (4-CBA).

In an embodiment the invention is mixture or composition comprising the alkyl-aromatic compound, a solvent, a bromine source, a catalyst, and ammonium acetate. The solvent comprises a carboxylic acid having from 1 to 7 carbon atoms. In an embodiment, the carboxylic acid comprises acetic acid. The solvent may contain more than one carboxylic acid. For example the solvent may further comprise benzoic acid. In another embodiment, the carboxylic acid of the solvent is acetic acid.

Optionally, the solvent may further comprise water. The water may be added to the mixture or generated in the mixture during the oxidation process. In an embodiment, the amount of water ranges from about 0.01 wt % to about 5 wt %, relative to the weight of the carboxylic acid having from 1 to 7 carbon atoms. The amount of water may range from about 0.1 wt % to about 2 wt %, relative to the weight of the carboxylic acid having from 1 to 7 carbon atoms. In an embodiment, the ratio of solvent to alkyl aromatic compound in the mixture ranges from about 1.5:1 to about 6:1 by weight. The ratio of solvent to alkyl aromatic compound may range from about 2:1 to about 4:1 by weight.

The catalyst comprises at least one of cobalt, manganese, titanium, chromium, copper, nickel, vanadium, iron, molybdenum, tin, cerium and zirconium. In an embodiment, the catalyst comprises cobalt and manganese. The metal may be in the form of an inorganic or organic salt. For example, the metal catalyst may be in the form of a carboxylic acid salt, such as, a metal acetate and hydrates thereof. Exemplary catalysts include cobalt (II) acetate tetrahydrate and manganese (II) acetate, individually or in combination. In an embodiment, the amount of manganese (II) acetate is less than the amount of cobalt (II) acetate tetrahydrate by weight.

The amount of catalyst used in the invention may vary widely. For example, the amount of cobalt may range from about 0.001 wt % to about 2 wt % relative to the weight of the solvent. In an embodiment, the amount of cobalt ranges from about 0.05 wt % to about 2 wt % relative to the weight of the solvent. The amount of manganese may range from about 0.001 wt % to about 2 wt % relative to the weight of the solvent. In an embodiment, the amount of manganese ranges from about 0.05 wt % to about 2 wt % relative to the weight of the solvent. In another embodiment, the ratio of cobalt to manganese ranges from about 3:1 to about 1:2 by weight on an elemental metal basis.

Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono- and di-bromoacetic acid, bromoacetyl bromide, tetrabromoethane, ethylene dibromide. In an embodiment, the bromine source comprises or consists essentially of or consists of hydrogen bromide. The amount of hydrogen bromide may range from about 0.01 wt % to about 5 wt %, relative to the weight of the solvent. In another embodiment, the amount of hydrogen bromide ranges from about 0.05 wt % to about 2 wt %, relative to the weight of the solvent.

The mixture also includes ammonium acetate. In an embodiment, the amount of ammonium acetate ranges from about 1 wt % to about 100 wt %, relative to the weight of the solvent. Thus, in a broad embodiment, the invention is a mixture comprising an alkyl-aromatic compound, a solvent, a bromine source, a catalyst, and ammonium acetate wherein the solvent comprises a carboxylic acid having from 1 to 7 carbon atoms and optionally water, and the catalyst comprises at least one of cobalt, titanium, manganese, chromium, copper, nickel, vanadium, iron, molybdenum, tin, cerium, and zirconium. In an embodiment, the mixture comprises an alkyl-aromatic compound, a solvent comprising acetic acid and optionally water, a bromine source comprising hydrogen bromide, a catalyst comprising cobalt and manganese, ammonium acetate.

In another embodiment, the invention is a process for oxidizing an alkyl-aromatic compound comprising: forming a mixture comprising the alkyl-aromatic compound, a solvent, a bromine source, a catalyst, and ammonium acetate; and contacting the mixture with an oxidizing agent at oxidizing conditions to produce an oxidation product comprising at least one of an aromatic aldehyde, an aromatic alcohol, an aromatic ketone, and an aromatic carboxylic acid. The solvent comprises a carboxylic acid having from 1 to 7 carbon atoms and optionally water, and the catalyst comprises at least one of cobalt, titanium, manganese, chromium, copper, nickel, vanadium, iron, molybdenum, tin, cerium, and zirconium. The mixture of the process may comprise an alkyl-aromatic compound, ammonium acetate, a solvent comprising acetic acid and optionally water, a bromine source comprising hydrogen bromide, a catalyst comprising cobalt and manganese.

Oxidation processes according to the invention may be practiced in laboratory scale experiments through full scale commercial operations. The process may be operated in batch, continuous, or semi-continuous mode. The mixture described above may be formed in various ways. The order of addition of the mixture components (e.g. alkyl-aromatic compound, solvent, bromine source, catalyst, and ammonium acetate) is not critical. In an embodiment, two or more components may be combined or mixed before being combined or mixed with other components. At least a portion of the mixture provides a liquid phase, though dissolution of one or more of the mixture components may not be complete at any or some time during the process. The liquid phase may be formed by mixing the components at ambient conditions. In another embodiment, the liquid phase is formed as the temperature of the mixture increases to the oxidation temperature. The mixture may be formed prior to the oxidation step, in the same or different vessel as that used in the oxidation step. In another embodiment, the mixture is formed in an oxidation reactor, e.g. adding various streams of the components individually and/or in combination to a continuous or semi-continuous oxidation reactor. The mixture, and/or various streams of the mixture components may be heated before they are mixed together.

Though many conventional alkyl aromatic oxidation processes are typically conducted in a mixed phase, and often include three phases (e.g. solid, gas, and liquid), they are frequently referred to in the art as "liquid phase" oxidation processes because the oxidation conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The process of the invention also comprises at least one step of contacting the mixture with an oxidizing agent at oxidizing conditions to produce an oxidation product comprising at least one of an aromatic aldehyde, an aromatic alcohol, an aromatic ketone, and an aromatic carboxylic acid. Thus, in another embodiment, the mixture further comprises an oxidizing agent. In yet another embodiment, the mixture further comprises an oxidation product comprising at least one of an aromatic aldehyde, an aromatic alcohol, an aromatic ketone, and an aromatic carboxylic acid. The oxidation product may comprise an aromatic carboxylic acid.

Suitable oxidizing agents for the process provide a source of oxygen atoms to oxidize the alkyl aromatic compound and/or an intermediate oxidation product at the oxidation conditions employed. Examples of oxidizing agents include peroxides, superoxides, and nitrogen compounds containing oxygen such as nitric acids. In an embodiment, the oxidizing agent is a gas comprising oxygen, e.g. air, carbon dioxide, and molecular oxygen. The gas may be a mixture of gasses. The amount of oxygen used in the process is preferably in excess of the stoichiometric amount required for the desired oxidation process. In an embodiment, the amount of oxygen contacted with the mixture ranges from about 1.2 times the stoichiometric amount to about 100 times the stoichiometric amount. Optionally, the amount of oxygen contacted with the mixture may range from about 2 times the stoichiometric amount to about 30 times the stoichiometric amount.

Oxidizing conditions generally include a temperature ranging from about 125° C. to about 275° C. and a pressure ranging from about atmospheric, i.e. 0 MPa(g), to about 6 MPa(g) and a residence time ranging from about 5 seconds to about 2 weeks. That is, the mixture has a temperature and a pressure within these ranges and may be maintained within these ranges for a period of time within the residence time range. In another embodiment, the temperature ranges from about 175° C. to about 225° C.; and the temperature may range from about 190° C. to about 235° C. In an embodiment, the pressure ranges from about 1.2 MPa(g) to about 6.0 MPa(g); and the pressure may range from about 1.5 MPa(g) to about 6.0 MPa(g). In a further embodiment, the residence time ranges from about 10 minutes to about 12 hours. The oxidation temperature, pressure and residence time may vary based on a variety of factors including for example, the reactor configuration, size, and whether the process is, batch, continuous, or semi-continuous. An oxidation condition may also vary based on other oxidation conditions. For example, use of a particular temperature range may enable use of a different residence time range.

In an embodiment, the oxidation product produced by the instant invention may precipitate, crystallize, or solidify in a liquid phase mixture at the oxidation conditions and/or as the mixture cools. Thus, a mixture according to the invention may further comprise a solid oxidation product. Other compounds, including color bodies, and other oxidation products may solidify with or be trapped in the solid oxidation product thus reducing the purity of the desired product. In an embodiment, the mixture comprises a liquid phase. The mixture may comprise a gas phase such as when the oxidizing agent is added as a gas. The mixture may comprise a solid phase e.g. a mixture component, an oxidation product, or a by-product fails to dissolve or solidifies in the mixture. In an embodiment, the mixture comprises a liquid phase, a solid phase and optionally a gas phase. In another embodiment, the mixture comprises a liquid phase and a gas phase.

As noted above and discussed below, it has been discovered that the invention may be used to produce a solid oxidation product having a different composition relative to those observed in conventional processes. In addition, the invention provides new ways to control the level of various contaminants in the solid oxidation product. In an embodiment, a process according to the invention further comprises forming the oxidation product as a solid, optionally at the oxidizing conditions, to produce the solid oxidation product and a mother liquor. The solid oxidation product may form as the mixture cools. The solid oxidation product may be separated from the mother liquor, i.e. liquid phase, and the mother liquor of the process may be recycled and reused in the contacting step or other steps of the process described below.

Processes according to the invention, may comprise one or more additional oxidizing steps. In an embodiment a second oxidation step includes a second oxidizing temperature that is lower than the temperature of the first oxidizing step. Processes according to the invention may include additional contacting steps of the invention as described herein, and/or the invention may be combined with other oxidizing steps such as conventional oxidizing steps known in the art. Multiple contacting or oxidation steps may be conducted in series and/or parallel and may be combined with other process steps such as purification steps described herein.

In a sequential embodiment, the invention includes a second oxidation step wherein a portion or all of the solid oxidation product, or the mother liquor, or both the solid oxidation product and the mother liquor produced in the first oxidation step forms a second mixture with a second solvent, a second bromine source, ammonium acetate, and a second catalyst. The second mixture is contacted with a second oxidizing agent at second oxidizing conditions to produce a second solid oxidation product comprising at least one of an aromatic aldehyde, an aromatic alcohol, an aromatic ketone, and an aromatic carboxylic acid. The second solvent comprises a carboxylic acid having from 1 to 7 carbon atoms, and the catalyst comprises at least one of cobalt, titanium, manganese, chromium, copper, nickel, vanadium, iron, molybdenum, tin, cerium, and zirconium. The second solvent, second bromine source, second catalyst, and second oxidation conditions may individually or collectively be the same or different from those of the first oxidation step. Optionally, a portion of the alkyl aromatic compound may be included in the second mixture. The optional elements and optional steps described for the first oxidation step above are equally applicable to this second oxidation step.

In a parallel embodiment, the invention further comprises a second oxidation step wherein a second mixture comprising a portion of the alkyl-aromatic compound, a second solvent, a second bromine source, and a second catalyst is formed. The second mixture is contacted with a second oxidizing agent at second oxidizing conditions to produce a second solid oxidation product comprising at least one of an aromatic aldehyde, an aromatic alcohol, an aromatic ketone, and an aromatic carboxylic acid. The second solvent comprises a carboxylic acid having from 1 to 7 carbon atoms and the second catalyst comprises at least one of cobalt, titanium, manganese, chromium, copper, nickel, vanadium, iron, molybdenum, tin, cerium, and zirconium. Optionally, the second mixture further comprises ammonium acetate. The second solvent, second bromine source, second catalyst, and second oxidation conditions may individually or collectively be the same or different from those of the first oxidation step. The optional elements and optional steps described for the first oxidation step above are equally applicable to this second oxidation step In another embodiment, the invention further comprises purifying the solid oxidation product. Purifying may comprise one or more additional steps to isolate and purify the solid oxidation product. Examples of purifying steps include:

separating wherein the solid oxidation product is separated from the mother liquor or another liquid phase such as by filtration and/or centrifugation; washing wherein the solid oxidation product is washed, for example with water and/or another solvent component; drying the solid oxidation product; and hydrogenation processes. Such additional processing steps have been described in the general literature and are well known to those of ordinary skill in the art to be used in various combinations to purify solid oxidation products of the invention. See for example, the references cited in this application and the art cited therein.

A purification step of instant invention may further comprise a one or more solvent contacting steps. A solvent contacting step comprises contacting a solid oxidation product, also including washed or dried solid oxidation products, with a second solvent comprising at least one of water, a carboxylic acid having from 1 to 7 carbon atoms, and a mother liquor to produce a second solid oxidation product. In an embodiment, the second solvent is selected from the group consisting of the mother liquor, a carboxylic acid having from 1 to 7 carbon atoms, water, and combinations thereof. Solvent contacting may leach impurities from the solid oxidation product, and/or the solid oxidation product may be partially or completely dissolved in the solvent. Solvent contacting conditions include a solvent contacting temperature. The solvent contacting temperature may be lower than the oxidation temperature. In an embodiment, the solvent contacting temperature is at least 20° C. lower than the oxidation temperature. Solvent contacting may be practiced for example in the one or more crystallizers that follow the oxidation reactor in some conventional processes. The second solid oxidation product may solidify, precipitate, or crystallize in the second solvent of the solvent contacting step.

In an embodiment, the invention is a process further comprising contacting the solid oxidation product and a solution comprising the mother liquor at contacting conditions including a second temperature to produce a second solid oxidation product and a second mother liquor; the second temperature being lower than the oxidation temperature. Optionally the process further comprises separating the second solid oxidation product from the second mother liquor; and the process may further comprise purifying the second solid oxidation product.

The solid oxidation product made by the instant invention may be purified by known methods including the use of a hydrogenation step. In an exemplary embodiment, a hydrogenation step is not required. In an embodiment, a process according to the invention includes one or more purification steps that exclude hydrogenation steps. That is, the purifying process steps may be selected from the group of process steps consisting of washing, separating, drying, solvent contacting, and combinations thereof.

EXAMPLES

The examples are presented to further illustrate some aspects and benefits of the invention and are not to be considered as limiting the scope of the invention.

Example 1

Experimental procedure: In a fume hood, load a Parr reactor with the specified amounts of components for the given experiment seal the reactor. The Parr reactor includes a gas distributor to disperse the gas through a 1.6 mm opening into the liquid, a mechanical gas entrainment stirrer, and baffles to ensure thorough mixing. Install the Parr reactor in a heater assembly at room temperature and connect a gas supply line to the reactor and a condenser to the reactor outlet. During operation, gases exit the reactor through the condenser then a trap, then a back-pressure regulator. Connect a safety vent having a rupture disk, and thermocouples to the reactor. Connect a cooling water recirculator to the condenser and begin to recirculate cooling water. Pressure test the Parr reactor at room temperature and 1.4 MPa(g) (200 psig) using nitrogen until there is no decrease in pressure for 15 minutes. Set the back pressure regulator on the reactor outlet to the experimental pressure and pressure test the reactor under nitrogen. Begin raising the reactor temperature to the experimental temperature under the nitrogen atmosphere. Always follow all instructions for the specific reactor including temperature and pressure limits. When the reactor reaches the desired temperature begin adding air at the experimental rate and monitor the reactor temperature and pressure for the duration of the test. During the test, the air flow into the reactor is maintained at 1250 standard $cm^3$ per minute, the pressure is maintained at 4.1 MPa(g), and the stirrer is maintained at 1600 rpm. At the end of the test shut off the heater, cut the air flow and allow the reactor to cool. When the reactor cools to less than about 35° C., open the back pressure valve, stop the cooling water, and remove and empty the reactor to obtain the solid oxidation product and mother liquor.

The mother liquor and products are filtered under vacuum to separate the solids and liquid. The solids are then mixed with approximately 100 cc deionized water at room temperature and decanted. The room temperature deionized water mixing and decanting is repeated two additional times. A fourth wash with deionized water is heated to approximately 95° C. for 30 minutes and then filtered. The solids are dried at 80° C. for 8-24 hours before analyzing.

Examples 2-3

Examples 2-3 were individual tests conducted using the equipment and procedure given in Example 1. The components of the mixture, given in grams, operating temperature and time, and results are given in Table 1.

TABLE 1

| Example Number | 2 | 3 |
|---|---|---|
| Oxidation Temperature, ° C. | 200 | 200 |
| Oxidation Time, hours | 6 | 6 |
| Mixture Components, grams | | |
| para-xylene | 20 | 20 |
| glacial acetic acid | 100 | 80 |
| water | 2 | 0.4 |
| ammonium acetate | 0 | 20 |
| hydrogen bromide | 0.4 | 0.4 |
| cobalt (II) acetate tetrahydrate | 0.8 | 0.8 |
| manganese (II) acetate | 0.6 | 0.6 |
| Analysis of solid product | | |
| terephthalic acid, wt % | 98.6 | 99.5 |
| 4-carboxybenzaldehyde, wt % | 1.10 | 0.37 |
| para-toluic acid, wt % | 0.26 | 0.07 |
| benzoic acid, ppm-wt | 230 | 0 |
| 4-hydoxymethylbenzoic acid, ppm-wt | 555 | 83 |

Example 2 (Comparative)

Conventional test run without ammonium acetate to demonstrate the level of impurities made using conventional solvents under standard oxidizing conditions.

Example 3

Same oxidizing conditions as Example 2 except ammonium acetate was substituted for some of the acetic acid. Incorporating ammonium acetate significantly increased the purity of the terephthalic acid and reduced the concentrations of 4-CBA, p-toluic acid, benzoic acid, and 4-hydoxymethyl-benzoic acid.

The invention claimed is:

1. A mixture for oxidizing an alkyl-aromatic compound comprising: the alkyl-aromatic compound, a solvent, a bromine source, a catalyst, and ammonium acetate, wherein the amount of ammonium acetate ranges from about 1 wt % to about 100 wt %, relative to the weight of the solvent; wherein the solvent comprises a carboxylic acid having from 1 to 7 carbon atoms, and optionally water, and the catalyst comprises at least one of cobalt, titanium, manganese, chromium, copper, nickel, vanadium, iron, molybdenum, tin, cerium, and zirconium.

2. The mixture of claim 1 further comprising an oxidizing agent.

3. The mixture of claim 1 wherein the carboxylic acid comprises acetic acid.

4. The mixture of claim 1 wherein the alkyl-aromatic compound is selected from the group consisting of toluene, para-xylene, ortho-xlyene, and meta-xylene.

5. The mixture of claim 1 wherein the catalyst comprises cobalt and manganese, optionally the catalyst has a ratio of cobalt to manganese ranging from about 3:1 to about 1:2 by weight on an elemental metal basis.

6. The mixture of claim 1 further comprising an oxidation product comprising at least one of an aromatic aldehyde, an aromatic alcohol, an aromatic ketone, and an aromatic carboxylic acid.

7. The mixture of claim 1 wherein the bromine source is at least one of HBr, NaBr, KBr, NH4Br, benzylbromide, mono-bromoacetic acid, di-bromoacetic acid, bromoacetyl bromide, tetrabromoethane, and ethylene di-bromide.

\* \* \* \* \*